United States Patent [19]

Levinson et al.

[11] Patent Number: 4,965,196
[45] Date of Patent: * Oct. 23, 1990

[54] POLYCISTRONIC EXPRESSION VECTOR CONSTRUCTION

[75] Inventors: Arthur D. Levinson, Burlingame; Christian Simonsen, San Jose, both of Calif.

[73] Assignee: Genentech, Inc., San Francisco, Calif.

[*] Notice: The portion of the term of this patent subsequent to Dec. 15, 2004 has been disclaimed.

[21] Appl. No.: 101,223

[22] Filed: Sep. 24, 1987

Related U.S. Application Data

[63] Continuation of Ser. No. 459,152, Jan. 19, 1983, Pat. No. 4,713,339.

[51] Int. Cl.$^5$ .................... C12P 21/00; C12N 15/00; C12N 9/06; C12N 5/00

[52] U.S. Cl. .................... 435/691; 435/69.3; 435/70.1; 435/70.3; 435/172.3; 435/191; 435/240.1; 435/240.2; 435/320; 935/32; 935/34; 935/36; 935/70

[58] Field of Search ................ 435/69.1, 172.1, 172.3, 435/69.3, 240.1, 240.2, 320, 191, 70.1, 70.3; 935/32, 34, 36, 70

Primary Examiner—James Martinell
Attorney, Agent, or Firm—Knobbe, Martens, Olson & Bear

[57] ABSTRACT

A method for controlled production of a desired mature protein in a vertebrate host cell through the use of a polycistronic expression vector, which contains sequences coding for the desired protein and a secondary protein, is described. Both coding sequences are governed by the same promoter and are separated by translational stop and start signal codons. The expression of the secondary sequence effects control over the expression of the sequence coding for the desired protein, and the secondary protein functions as a marker for selection of transfected cells.

16 Claims, 4 Drawing Sheets

POLYCISTRONIC EXPRESSION VECTOR CONSTRUCTION

This application is a continuing application under 35 U.S.C. 120/121 of application Ser. No. 06/459,152, filed Jan. 19, 1983, now U.S. Pat. No. 4,713,339.

BACKGROUND OF THE INVENTION

This invention relates to the application of recombinant DNA technology to the production of polypeptide in vertebrate cell cultures. More specifically, this invention relates to utilizing the coding sequence for a secondary control polypeptide as a tool in controlling production of a foreign polypeptide by the vertebrate cell culture.

The general principle of utilizing a host cell for the production of a heterologous protein—i.e., a protein which is ordinarily not produced by this cell—is well known. However, the technical difficulties of obtaining reasonable quantities of the heterologous protein by employing vertebrate host cells which are desirable by virtue of their properties with regard to handling the protein formed are many. There have been a number of successful examples of incorporating genetic material coding for heterologous proteins into bacteria and obtaining expression thereof. For example, human interferon, desacetyl-thymosin alpha-1, somatostatin, and human growth hormone have been thus produced. Recently, it has been possible to utilize non-bacterial hosts such as yeast cells (see, e.g., co-pending application, U.S. Ser. No. 237,913, filed Feb. 25, 1981;) and vertebrate cell cultures (U.S. application Ser. No. 298,235, filed Aug. 31, 1981) as hosts. The use of vertebrate cell cultures as hosts in the production of mammalian proteins is advantageous because such systems have additional capabilities for modification, glycosylation, addition of transport sequences, and other subsequent treatment of the resulting peptide produced in the cell. For example, while bacteria may be successfully transfected and caused to express "alpha thymosin", the polypeptide produced lacks the N-acetyl group of the "natural" alpha thymosin found in mammalian system.

In general, the genetic engineering techniques designed to enable host cells to produce heterologous proteins include preparation of an "expression vector" which is a DNA sequence containing, (1) a "promoter", i.e., a sequence of nucleotides controlling and permitting the expression of a coding sequence;

(2) a sequence providing mRNA with a ribosome binding site;

(3) a "coding region", i.e., a sequence of nucleotides which codes for the desired polypeptide; and (4) a "termination sequence" which permits transcription to be terminated when the entire code for the desired protein has been read; and (5) if the vector is not directly inserted into the genome, a "replicon" or origin of replication which permits the entire vector to be reproduced once it is within the cell.

In the construction of vectors in the present invention, the same promoter controls two coding sequences, one for a desired protein, and the other for a secondary protein. Transcription termination is also shared by these sequences. However, the proteins are produced in discrete form because they are separated by a stop and start translational signal.

Ordinarily, the genetic expression vectors are in the form of plasmids, which are extrachromosomal loops of double stranded DNA. These are found in natural form in bacteria, often in multiple copies per cell. However, artificial plasmids can also be constructed, (and these, of course, are the most useful), by splicing together the four essential elements outlined above in proper sequence using appropriate "restriction enzymes". Restriction enzymes are nucleases whose catalytic activity is limited to lysing at a particular base sequence, each base sequence being characteristic for a particular restriction enzyme. By artful construction of the terminal ends of the elements outlined above (or fractions thereof) restriction enzymes may be found to splice these elements together to form a finished genetic expression vector.

It then remains to induce the host cell to incorporate the vector (transfection), and to grow the host cells in such a way as to effect the synthesis of the polypeptide desired as a concomitant of normal growth.

Two typical problems are associated with the above-outlined procedure. First, it is desirable to have in the vector, in addition to the four essential elements outlined above, a marker which will permit a straightforward selection for those cells which have, in fact, accepted the genetic expression vector. In using bacterial cells as hosts, frequently used markers are resistance to an antibiotic such as tetracycline or ampicillin. Only those cells which are drug resistant will grow in cultures containing the antibiotic. Therefore, if the cell culture which has been sought to be transfected is grown on a medium containing the antibiotic, only the cells actually transfected will appear as colonies. As the frequency of transformation is quite low (approximately 1 cell in $10^6$ being transfected under ideal conditions) this is almost an essential prerequisite as a practical matter.

For vertebrate cells as hosts, the transformation rate achieved is more efficient (about 1 cell in $10^3$). However, facile selection remains important in obtaining the desired transfected cells. Selection is rendered important, also, because the rate of cell division is about fifty times lower than in bacterial cells—i.e., although E coli divide once in about every 20-30 minutes, human tissue culture cells divide only once in every 12 to 24 hours.

The present invention, in one aspect, addresses the problem of selecting for vertebrate cells which have taken up the genetic expression vector for the desired protein by utilizing expression of the coding sequence for a secondary protein, such, for example, as an essential enzyme in which the host cell is deficient. For example, dihydrofolate reductase (DHFR) may be used as a marker using host cells deficient in DHFR.

A second problem attendant on production of polypeptides in a foreign host is recovery of satisfactory quantities of protein. It would be desirable to have some mechanism to regulate, and preferably enhance, the production of the desired heterologous polypeptide. In a second aspect of the invention, a secondary coding sequence which can be affected by externally controlled parameters is utilized to allow control of expression by control of these parameters. Furthermore, provision of both sequences on a polycistron in itself permits selection of transformants with high expression levels of the primary sequence.

It has been shown that DHFR coding sequences can be introduced into, expressed in, and amplified in mammalian cells. Genomic DNA from methotrexate resistant Chinese Hamster Ovary (CHO) cells has been introduced into mouse cells and results in transformants which are also resistant to methotrexate (1). The mechanism by which methotrexate (MTX) resistance in mouse cells is developed appears to be threefold: through gene amplification of the DHFR coding sequence (2,3,4); through decrease in uptake of MTX (5,6) and through reduction in affinity of the DHFR produced for MTX (7).

It appears that amplification of the DHFR gene through MTX exposure can result in a concomitant amplification of a cotransfected gene sequence. It has also been shown that mouse fibroblasts, transfected with both a plasmid containing hepatitis B DNA sequences, and genomic DNA from a hamster cell line containing a mutant gene for MTX-resistant DHFR, secrete increased amounts of hepatitis B surface antigen (HBsAg) into the medium when MTX is employed to stimulate DHFR sequence amplification (8). Further, mRNA coding for the E.coli protein XGPRT is amplified in the presense of MTX in CHO cells co-transfected with the DHFR and XGPRT gene sequences under control by independent promoters (9). Finally, increased expression of a sequence endogenous to the promoter in a DHFR/SV40 plasmid combination in the presence of MTX has been demonstrated (10).

SUMMARY OF THE INVENTION

The present invention is based on the discovery that, in vertebrate cell hosts, where the genetic expression vector for a desired polypeptide contains a secondary genetic coding sequence under the control of the same promoter, this secondary sequence provides for a convenient screening marker, both for transformants in general, and for transformants showing high expression levels for the primary sequence, as well as serving as a control device whereby the expression of a desired polypeptide can be regulated, most frequently enhanced.

This is particularly significant as the two proteins, according to the method of this invention, are produced separately in mature form. While both DNA coding sequences are controlled by the same transcriptional promoter, so that a fused message (mRNA) is formed, they are separated by a translational stop signal for the first and start signal for the second, so that two independent proteins result.

As a vertebrate host cell culture system is often advantageous because it is capable of glycosylation, phosphorylation, and lipid association appropriate to animal systems, (whereas bacterial hosts are not), it is significant that marker systems and regulating systems can be provided within this context.

Accordingly, one aspect of the invention is a method for obtaining useful heterologous proteins from vertebrate cell host cultures through the use of a polycistronic expression vector which contains sequences coding for a secondary protein and a desired protein, wherein both the desired and secondary sequences are governed by the same promoter. The coding sequences are separated by translational stop and start signal codons. The expression of the secondary sequence effects control over the expression of the sequence for the desired protein, and the secondary protein functions as a marker for selection of transfected cells. The invention includes use of secondary sequences having either or both of these effects.

In other aspects, the invention concerns the genetic expression vectors suitable for transfecting vertebrate cells in order to produce the desired heterologous peptide, the cell culture produced by this transfection, and the polypeptide produced by this cell culture.

DETAILED DESCRIPTION AND DESCRIPTION OF THE PREFERRED EMBODIMENT

A. Definitions

As used herein,

"Plasmids" includes both naturally occurring plasmids in bacteria, and artificially constructed circular DNA fragments.

"Expression vector" means a plasmid which contains at least the four essential elements set forth hereinabove for the expression of the heterologous peptide in a host cell culture.

"Heterologous protein" means a protein or peptide which is not normally produced by, or required for the viability of, the host organism.

"Desired protein" means a heterologous protein or peptide which the method of the invention is designed to produce.

"Secondary peptide" means the protein or peptide which is not the heterologous peptide desired as the primary product of the expression in the host cell, but rather a different heterologous peptide which, by virtue of its own characteristics, or by virtue of the characteristics of the sequence coding for it is capable of "marking" transfection by the expression vector and/or regulating the expression of the primarily desired heterologous peptide.

The peptide sequence may be either long or short ranging from about 5 amino acids to about 1000 amino acids. The conventional distinction between the words peptide and protein is not routinely observed in the description of the invention. If the distinction is to be made, it will be so specified.

"Primary sequence" is the nucleotide sequence coding for the desired peptide, and "Secondary Sequence" means a sequence of nucleotides which codes for the secondary peptide.

"Transfection" of a host cell means that an expression vector has been taken up by the host cell in a detectable manner whether or not any coding sequences are in fact expressed. In the context of the present invention, successful transfection will be recognized when any indication of the operation of this vector within the host cell is realized It is recognized that there are various levels of success within its context. First, the vector's coding sequence may or may not be expressed. If the vector is properly constructed with inclusion of promoter and terminator, however, it is highly probable that expression will occur. Second, if the plasmid representing the vector is taken up by the cell and expressed, but fails to be incorporated within the normal chromosomal material of the cell, the ability to express this plasmid will be lost after a few generations. On the other hand, if the vector is taken up within the chromosome, the expression remains stable through repeated replications of the host cell. There may also be an intermediate result. The precise details of the manner in which transfection can thus occur are not understood, but it is clear that a continuum of outcomes is found experimentally in terms of the stability of the expression over several generations of the host culture.

B. A Preferred Embodiment of the Desired Peptide

In a preferred specific embodiment, exemplary of the invention herein, the primary genetic sequence encodes the hepatitis B-surface antigen (HBsAg). This protein is derived from hepatitis B virus, the infective agent of hepatitis B in human beings. This disease is characterized by debilitation, liver damage, primary carcinoma, and often death. The disease is reasonably widespread especially in many African and Asian countries, where many people are chronic carriers with the potential of transmitting the disease pandemically. The virus (HBV) consists of a DNA molecule surrounded by a nuclear capsid, in turn surrounded by an envelope. Proteins which are associated with the virus include the surface antigen (HBsAg), a core antigen, and a DNA polymerase. The HBsAg is known to produce antibodies in infected people. HBsAg found in the serum of infected individuals consists of protein particles which average ca. 22 nanometers in diameter, and are thus called "22 nanometer particles". Accordingly, it is believed that the HBsAg particle would be an effective basis for a vaccine.

C. A Preferred Embodiment of the Secondary Peptide

It has been recognized that environmental conditions are often effective in controlling the quantity of particular enzymes that are produced by cells under certain growth conditions. In the preferred embodiment of the present invention, advantage is taken of the sensitivity of certain cells to methotrexate (MTX) which is an inhibitor of dihydrofolate reductase (DHFR). DHFR is an enzyme which is required, indirectly, in synthesis reactions involving the transfer of one carbon units. Lack of DHFR activity results in inability of cells to grow except in the presence of those compounds which otherwise require transfer of one carbon units for their synthesis. Cells lacking DHFR, however, will grow in the presence of a combination of glycine, thymidine and hypoxanthine.

Cells which normally produce DHFR are known to be inhibited by methotrexate. Most of the time, addition of appropriate amounts of methotrexate to normal cells will result in the death of the cells. However, certain cells appear to survive the methotrexate treatment by making increased amounts of DHFR, thus exceeding the capacity of the methotrexate to inhibit this enzyme (2,3,4). It has been shown previously that in such cells, there is an increased amount of messenger RNA coding for the DHFR sequence. This is explained by assuming an increase in the amount of DNA in the genetic material coding for this messenger RNA. In effect, apparently the addition of methotrexate causes gene amplification of the DHFR gene. Genetic sequences which are physically connected with the DHFR sequence although not regulated by the same promoter are also amplified (1,8,9,10). Consequently, it is possible to use the amplification of the DHFR gene resulting from methotrexate treatment to amplify concomitantly the gene for another protein, in this case, the desired peptide.

Moreover, if the host cells into which the secondary sequence for DHFR is introduced are themselves DHFR deficient, DHFR also serves as a convenient marker for selection of cells successfully transfected. If the DHFR sequence is effectively connected to the sequence for the desired peptide, this ability serves as a marker for successful transfection with the desired sequence as well.

D. Vector Construction Techniques Employed (Materials and Methods)

The vectors constructed in the Examples set forth in E are constructed by cleavage and ligation of isolated plasmids or DNA fragments.

Cleavage is performed by treating with restriction enzyme —(or enzymes) in suitable buffer. In general, about 20 μg plasmid or DNA fragments require about 1-5 units of enzyme in 200 μl of buffer solution. (Appropriate buffers for particular restriction enzymes are specified by the manufacturer.) Incubation times of about 1 hour at 37° C. are workable. After incubations, protein is removed by extraction with phenol and chloroform, and the nucleic acid recovered from the aqueous fraction by precipitation with ethanol.

If blunt ends are required, the preparation is treated for 15 minutes at 15° with 10 units of Polymerase I (Klenow), phenol-chlorform extracted, and ethanol precipitated.

Size separation of the cleaved fragments is performed using 6 percent polyacrylamide gel described by Goeddel, D., et al., Nucleic Acids Res, 8: 4057 (1980) incorporated herein by reference.

For ligating approximately equimolar amounts of the desired components, suitably end tailored to provide correct matching are treated with about 10 units T4 DNA ligase per 0.5 μg DNA.

E. Detailed Description of a Preferred Embodiment:

In general, the expression vector suitable for the present invention is constructed by adaptation of gene splicing techniques. The starting material is a naturally occurring bacterial plasmid, previously modified, if desired. A preferred embodiment of the present invention utilizes a pML plasmid which is a modified pBR 322 plasmid prepared according to Lusky, M. et al. Nature 239: 79 (1981) which is provided with a single promoter, derived from the simian virus SV-40 and the coding sequence for DHFR and for HBsAg.

In the construction, the promoter (as well as a ribosome binding sequence) is placed upstream from the coding sequence coding for a desired protein and one coding for a secondary protein. A single transcription termination sequence is downstream from both. At the end of the upstream code sequence is placed a translational stop signal; a translational start signal begins the downstream sequence. Thus, expression of the two coding sequences results in a single mRNA strand, but two separate mature proteins.

In a particularly preferred embodiment, the sequence coding for the secondary peptide is downstream from that coding for the desired peptide. Under these circumstances, procedures designed to select for the cells transformed by the secondary peptide will also select for particularly enhanced production of the desired peptide.

F. Examples

The following examples are intended to illustrate, but not limit the invention.

EXAMPLE 1

Vector Containing the HBsAg Sequence, pE342 HS94.HBV

Figure 1:
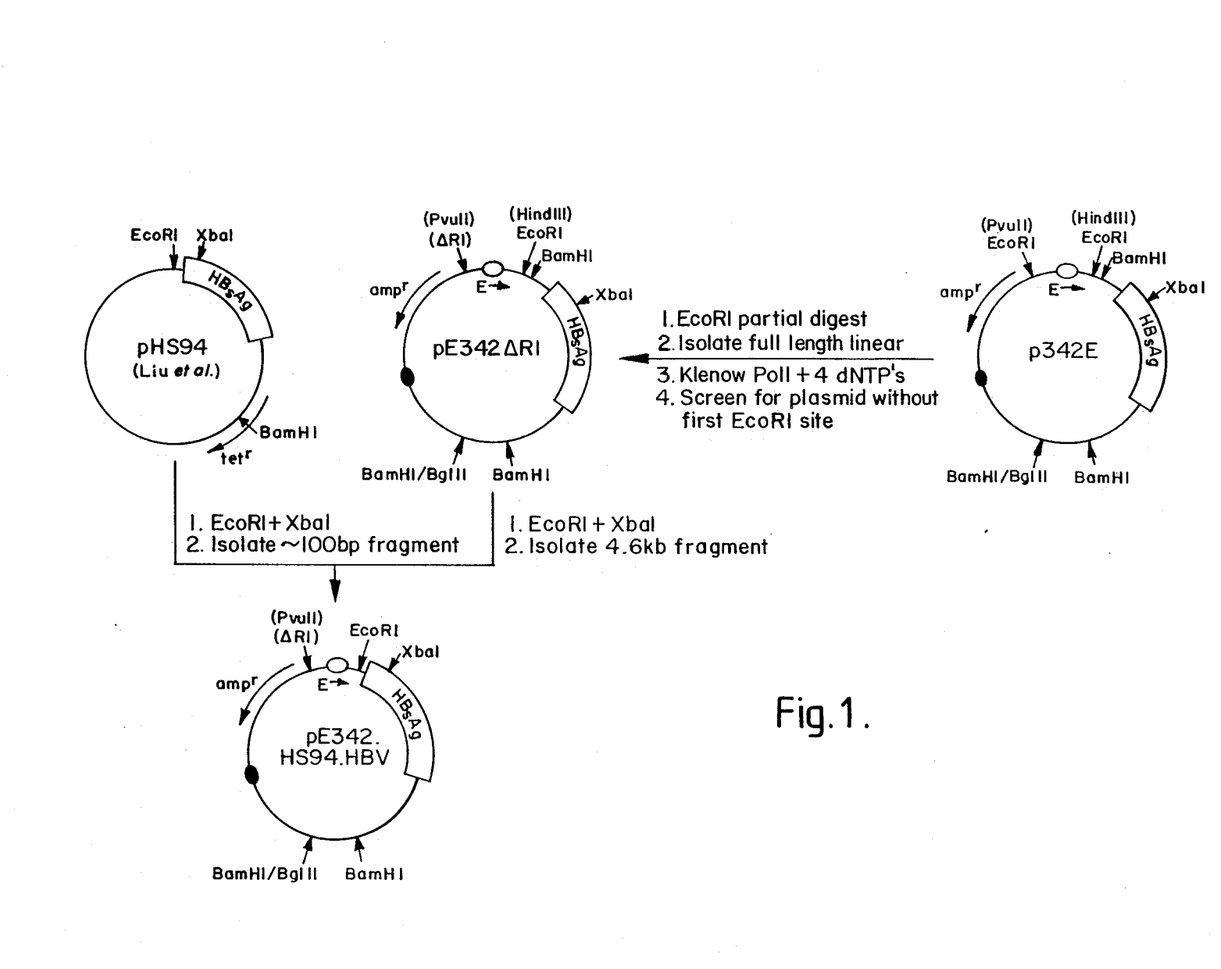
FIG. 1 shows the cons of an expression vector for HBsAg, pE342.HS94.HBV.

FIG. 1 shows the construction of the HBsAg plasmid.

The 1986 bp Eco R1-BgIII fragment which spans the surface antigen gene was isolated from the HBV viral genome cloned with pBR322 as described by Liu, et al., *DNA*, 1: 213 (1982), incorporated herein by reference. This sequence was ligated between the Eco RI and Bam HI sites of pML, a pBR322 derivative which lacks sequences inhibitory to its replication in simian cells, as described by Lusky, et al., *Nature*, 293: 79 (1981), incorporated herein by reference. Into the single Eco RI site of the resulting plasmid was inserted the 342 bp origin fragment of SV40 obtained by Hind III Pvu II digestion of the virus genome, which had been modified to be bounded by Eco RI restriction sites resulting in p342E (also referred to as pHBs348-E) as described by Levinson et al., patent application Ser. No. 326,980, filed Dec. 3, 1981, which is hereby incorporated by reference. The 5' nontranslated leader region of HBsAg was removed by treatment with Eco RI and with Xba, and the analogous 150 bp Eco RI-Xba fragment of a hepatitis expression plasmid pHS94 Liu, et al, (supra) was inserted in its place to create pE342.HS94.HBV.

(As described by Liu, et al. pHS94 contains the translational start codon of the authentic HBsAg gene, but lacks all 5' nontranslated message sequences. The levels of expression of both the authentic EcoR I-Bgl II and pHS94 derived equivalent under control of the SV40 early promoter as described above are equivalent and are interchangeable without affecting the performance of the plasmid.)

EXAMPLE 2

Vector Containing the DHFR Sequence, pE342.D22

Figure 2:
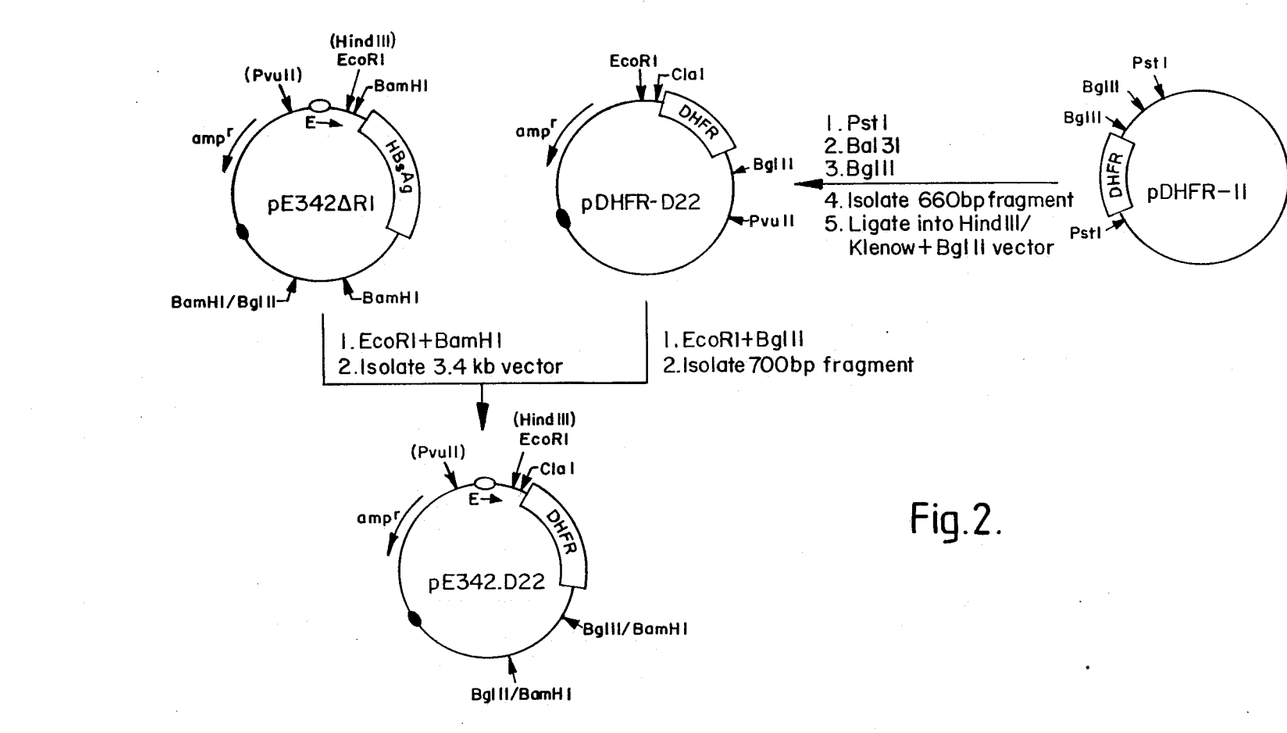
FIG. 2 shows the construction of an expression vector for DHFR, pE342.D22.

A plasmid carrying DHFR as the only expressable sequence is pE348.D22, the construction of which shown in FIG. 2.

The 1600 bp Pst I insert of the DHFR cDNA plasmid DHFR-11 Nunberg, et al., *Cell*, 19: 355 (1980) was treated with the exonuclease Bal 31 in order to remove the poly G:C region adjacent to the Pst I sites, digested with Bgl II and the resulting fragments of approximately 660 bp isolated from gels. The Bal31-Bgl II digested cDNA was ligated into a pBR322 plasmid derivative containing a Bgl II site. (Following digestion of pBR322 with Hind III, the plasmid fragment was filled in using Klenow DNA polymerase in the presence of the four deoxynucleotide triphosphates, and subcut with Bgl II.) The resulting plasmid, pDHFR-D22, has an EcoR I site situated 29 bp upstream of the fusion site between pBR322 and the 5' end of the DHFR cDNA. The EcoR I-Bgl II fragment encompassing the coding sequences of the cDNA insert was then excised from pDHFR-D22 and ligated to EcoR I-BamH I digested pE342 HBV (Example 1), creating the DHFR expression plasmid pE342.D22.

EXAMPLE 3

Vectors Containing Both DHFR and HBsAg Sequences

Two such vectors were constructed, pE342.HBV.D22 containing a polycistron wherein the DHFR gene is downstream from the HBsAg gene, and pE342.HBV.E400.D22, (FIG. 3) in which the genes coding for DHFR and HBsAg are not polycistronic.

Figure 3:
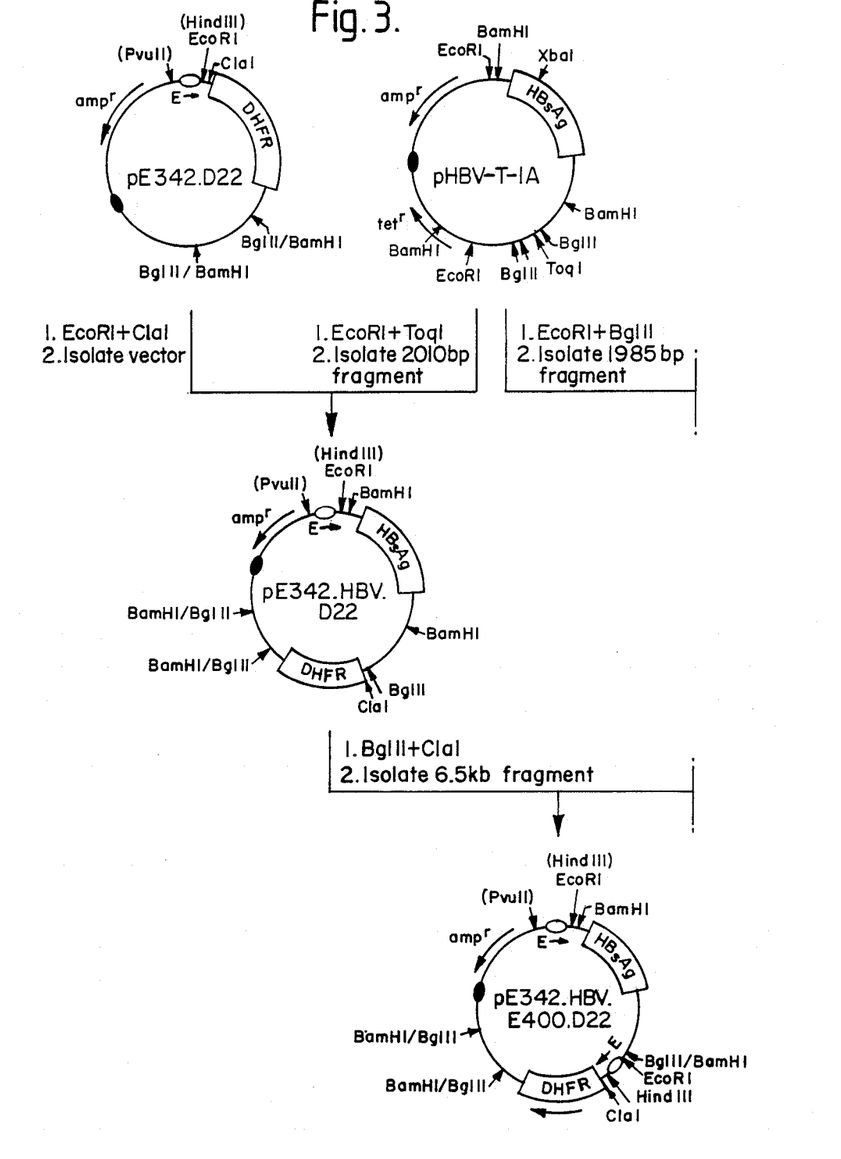
FIG. 3 shows the construction of an expression vectors for DHFR and HBsAg, pE342.HBV.D22 and pE342.HBV.E400.D22.

A. pE342.HBV.D22 was constructed by ligating the EcoR I-Taq I fragment of cloned HBV DNA (Liu,.et al. (supra)), to EcoR I-Cla I digested pE342 D22.

B. This plasmid was further modified by fusing an additional SV40 early promoter between the Bgl II site and the Cla I site of the DHFR insert of pE342.HBV.D22, creating pE342 HBV.E400.D22.

HBV viral DNA contains a single Taq I site 20 bp beyond the Bgl II site that was used to generate the EcoR I-Bgl II fragment encompassing the surface antigen gene. Thus, EcoR I and Taq I digestion of cloned HBV viral DNA results in a fragment of ~2000 bp spanning the surface antigen gene, and containing a single Bgl II site (1985 bp from the EcoR I site, (Liu, et al (supra)). (The ends of DNA fragments Taq I and Cla I generated by digestion are cohesive, and will ligate together).

The Cla I site is regenerated; thus pE342.HBV.D22 contains both a Bgl II and Cla I site, which are situated immediately in front of the DHFR coding sequences.

An SV40 origin bounded by restriction sites cohesive with the Bgl II and Cla I sites of pE342.HBV.D22 was constructed by digesting SV40 DNA with Hpa II, filling in as described above, and subcutting with Hind III. A 440 bp fragment spanning the origin was isolated. This was ligated, in a tripartite ligation, to the 4000 bp pBR322 fragment generated by Hind III and BamH I digestion, and the 1986 bp fragment spanning the surface antigen gene generated by digesting the cloned HBV viral DNA with EcoR I, filling in with Klenow DNA polymerase 1, subdigesting with Bgl II, and isolating on an acrylamide gel. Ligation of all three fragments is achievable only by joining of the filled in Hpa II with EcoR I, the two Hind III sites with each other and the Bgl II with BamH I. Thus when the resulting plasmid is restricted with ClaI and BamH I, a 470 bp fragment is obtained which contains the SV40 origin. This fragment is inserted into the Cla I and Bgl II sites of pE342.HBV.D22, (paragraph A) creating pE342.HBV.E400.D22 (FIG. 3).

EXAMPLE 4

Transfection of Host Cells

The host cells herein are vertebrate cells grown in tissue culture. These cells, as is known in the art, can be maintained as permanent cell lines prepared by successive serial transfers from isolated normal cells. These cell lines are maintained either on a solid support in liquid medium, or by growth in suspensions containing support nutrients.

In the preferred embodiment, CHO cells, which were deficient in DHFR activity are used. These cells are prepared and propagated as described by Urlaub and Chasin, *Proc. Natl. Acad. Sci. (USA)*, 77:4216 (1980), which is incorporated herein by reference.

The cells are transfected with 5 mg of desired vector as prepared above using the method of Graham and Van Der Eb, *Virology*, 52: 456 (1978) incorporated herein by reference.

The method insures the interaction of a collection of plasmids with a particular host cell, thereby increasing the probability that if one plasmid is absorbed by a cell, additional plasmids would be absorbed as well. Accordingly, it is practicable to introduce both the primary and secondary coding sequences using separate vectors for each, as well as by using a single vector containing both sequences.

EXAMPLE 5

Growth of Transfected Cells and Expression of Peptides

The CHO cells which were subjected to transfection as set forth above were first grown for two days in non-selective medium, then the cells were transferred into medium lacking glycine, hypoxanthine, and thymidine, thus selecting for cells which are able to express the plasmid DHFR. After about 1-2 weeks, individual colonies were isolated with cloning rings.

Cells were plated in 60 or 100 mm tissue culture dishes at approximately $0.5 \times 10^6$ cells/dish. After 2 days growth, growth medium was changed. HBsAg was assayed 24 hours later by RIA (Ausria II, Abbott). Cells were counted and HBsAg production standardized on a per cell basis. 10-20 random colonies were analyzed in this fashion for each vector employed.

In one example of the practice of the invention, the following results were obtained:

| Vector | Transfectional efficiency of Dhfr$^-$ cells (colonies/ug/$10^6$ cells) | HBsAg production; ng/$10^6$ cells/day (Percent of colonies in given range) | | | | | |
|---|---|---|---|---|---|---|---|
| | | 0 | 0-10 | 10-100 | 100-500 | 500-1500 | >1500 |
| pE342.D22 | 935 | 100 | 0 | 0 | 0 | 0 | 0 |
| pE342.HS94 | <.2 | 1 | 1 | 1 | 1 | 1 | 1 |
| pE342.D22 + pE342.HS94 | 340 | 0 | 50 | 30 | 20 | 0 | 0 |
| pE342.HBV.D22 | 20 | 0 | 0 | 0 | 0 | 55 | 45 |
| pE342.HBV.E400.D22 | 510 | 0 | 17 | 17 | 58 | 8 | 0 |

The production of surface antigen in several of the highest expressing cell lines has been monitored for greater than 20 passages and is stable. The cells expressing the surface antigen remain attached to the substratum indefinitely and will continue to secrete the large amounts of surface antigen as long as the medium is replenished.

It is clear that the polycistronic gene construction results in isolation of the cells producing the highest levels of HBsAg. 100 percent of colonies transformed with pE342.HBV.D22 produced over 500 ng/$10^6$ cells/day whereas 92 percent of those transformed with the non-polycistronic plasmid pE342.HBV.E400.D22 produced less than that amount. Only cells from the polycistronic transfection demonstrated production levels of more than 1500 ng/$10^6$ cells/day.

EXAMPLE 6

Treatment with Methotrexate

The surface antigen expressing cell lines are inhibited by methotrexate (MTX), a specific inhibitor of DHFR at concentrations greater than 10 nM. Consistent with previous studies on the effects of MTX on tissue culture cells, occasional clones arise which are resistent to higher concentrations (50 nM) of MTX at a frequency of approximately $10^{-5}$. However, these clones no longer produce surface antigen despite the amplification of HBV sequences in the MTX resistant clones. Thus, the HBV gene is amplified, though expression falls off in this case. This suggests that further production of surface antigen may be lethal to the cell.

EXAMPLE 7

Recovery of Desired Peptide

The surface antigen produced is in the form of a particle, analogous to the 22 nm particle observed in the serum of patients infected with the virus. This form of antigen has been shown to be highly immunogenic. When the cells are grown in medium lacking calf serum or other supplements, approximately 10 percent of the protein contained in the medium is surface antigen and this protein can be isolated by methods known in the art. The surface antigen comigrates on SDS-polyacrylamide gels with the 22 nm particle derived protein.

REFERENCES

1. Wigler, M., et al, *Proc. Natl. Acad. Sci.*, 77: 3567 (1980)
2. Schimke, Robert T., et al, *Science*, 202: 1051 (1978)
3. Biedler, J. L., et al, *Cancer Res.*, 32: 153 (1972)
4. Chang, S. E., et al, *Cell*, 7: 391 (1976)
5. Fischer, G. A., *Biochem Pharmacol.*, 11: 1233 (1962)
6. Sirotnak, F. M., et al, *Cancer Res.*, 28: 75 (1968)
7. Flintoff, W. F., et al, *Somat. Cell. Genet.*, 2: 245 (1976)
8. Christman, J., et al., *Proc. Natl. Acad. Sci.*, 79: 1815 (1982)
9. Ringold, Gordon, et al., *J. Molec and Appl. Gen.*, 1: 165 (1981)
10. Kaufman, R. F., et al., *J. Molec. Biol.*, 159: 601 (1982)
11. Perucho, Manuel, et al., *Cell*, 22:309 (1980)

What is claimed is:

1. A method for producing a desired mature protein in a vertebrate host cell, which method comprises:
   (a) providing an expression vector which vector comprises
      (i) a DNA sequence which codes for the desired protein and
      (ii) a DNA sequence which codes for a secondary protein wherein each of the sequences (i) and (ii) is operably linked to the same promoter, and separated by a translational stop signal, and a translational start signal;
   (b) transfecting a vertebrate host cell culture with the vector described in (a); and
   (c) allowing the host cell culture to grow under conditions favorable to the production of the secondary protein.

2. The method of claim 1 wherein the secondary protein is DHFR.

3. The method of claim 1 wherein the desired protein is HBsAg.

4. The method of claim 2 wherein the desired protein is HBsAg.

5. The method of claim 1 wherein the host cells are CHO cells.

6. The method of claim 2 wherein the host cells are deficient in DHFR.

7. The method claim 6 wherein the host cells are CHO cells.

8. The method of claim 2 wherein the transfected host cell culture is grown in the presence of a DHFR inhibitor.

9. The method of claim 8 wherein the inhibitor is methotrexate.

10. A method for controlling the production of a desired protein in a host cell, which method comprises:
   (a) transfecting said host cells with an expression vector containing the coding sequences for a secondary protein and for the desired protein, both sequences operably linked to the same promoter sequence, and separated by a translational stop signal and a translational start signal;
   (b) culturing the cells by adjusting externally controlled parameters to cause amplification of the sequence for the secondary protein.

11. A method for selecting vertebrate cells which have been transfected with an expression vector capable of expressing a desired protein which method comprises:
   treating cells with a vector containing coding sequences for both the desired protein and a secondary protein, and
   growing the cells under culture conditions requiring the presence of the secondary protein for the growth of the host cells;
   wherein both coding sequences are operably linked to the same promoter sequence and separated by translational stop and start codons.

12. The method of claim 11 wherein the secondary protein is DHFR.

13. The method of claim 12 wherein the culture conditions comprise a medium lacking glycine, hypoxanthine, and thymidine.

14. A method for selecting vertebrate cells which produce high levels of a desired heterologous protein, which method comprises:
   transfecting the cells with a vector containing the coding sequences for the desired protein and, downstream therefrom, for a secondary protein; and
   growing the cells under culture conditions allowing for selection of the transfected cells by utilizing expression of the coding sequence for the secondary protein;
   wherein both coding sequences are operably linked to the same promoter sequence and separated by translational stop and start signals.

15. The method of claim 14 wherein the secondary protein is DHFR.

16. The method of claim 15 wherein the culture conditions allowing for selection comprise a medium lacking glycine, hypoxanthine, and thymidine.

* * * * *